United States Patent
Gu et al.

(10) Patent No.: US 10,292,925 B2
(45) Date of Patent: May 21, 2019

(54) PEG FREE STABLE LOW VISCOSITY OIL-IN-WATER EMULSION AND USE THEREOF

(71) Applicants: Evonik Specialty Chemicals (Shanghai) Co., Ltd., Shanghai (CN); Evonik Degussa GmbH, Essen (DE)

(72) Inventors: Yinghua Gu, Shanghai (CN); Haizhou Zhang, Singapore (SG); Achim Friedrich, Hattingen (DE); Juergen Meyer, Essen (DE); Verena Dahl, Kürten (DE); Juan Chu, Shanghai (CN); Jan Marian von Hof, Essen (DE)

(73) Assignees: Evonik Specialty Chemicals (Shanghai) Co., Ltd., Shanghai (CN); Evonik Degussa GmbH, Essen (DE)

( * ) Notice: Subject to any disclaimer, the term of this patent is extended or adjusted under 35 U.S.C. 154(b) by 0 days.

(21) Appl. No.: 15/549,183

(22) PCT Filed: Mar. 13, 2015

(86) PCT No.: PCT/CN2015/074181
§ 371 (c)(1),
(2) Date: Aug. 7, 2017

(87) PCT Pub. No.: WO2016/145561
PCT Pub. Date: Sep. 22, 2016

(65) Prior Publication Data
US 2018/0036218 A1    Feb. 8, 2018

(51) Int. Cl.
| | | |
|---|---|---|
| *A61K 8/02* | (2006.01) | |
| *A61K 8/04* | (2006.01) | |
| *A61K 8/06* | (2006.01) | |
| *A61K 8/39* | (2006.01) | |
| *A61K 8/49* | (2006.01) | |
| *A61K 8/60* | (2006.01) | |
| *A61K 8/86* | (2006.01) | |
| *A61K 9/00* | (2006.01) | |
| *A61K 9/06* | (2006.01) | |
| *C08L 5/00* | (2006.01) | |
| *A61K 47/14* | (2017.01) | |
| *A61K 9/107* | (2006.01) | |
| *A61Q 17/04* | (2006.01) | |
| *A61Q 19/00* | (2006.01) | |

(52) U.S. Cl.
CPC ............ *A61K 8/604* (2013.01); *A61K 8/0208* (2013.01); *A61K 8/046* (2013.01); *A61K 8/062* (2013.01); *A61K 8/39* (2013.01); *A61K 8/4973* (2013.01); *A61K 8/86* (2013.01); *A61K 9/0014* (2013.01); *A61K 9/06* (2013.01); *A61K 9/107* (2013.01); *A61K 47/14* (2013.01); *A61Q 17/04* (2013.01); *A61Q 19/00* (2013.01); *C08L 5/00* (2013.01); *A61K 2800/21* (2013.01); *A61K 2800/30* (2013.01); *A61K 2800/48* (2013.01)

(58) Field of Classification Search
CPC ............ A61K 2800/21; A61K 2800/30; A61K 2800/48; A61K 47/14; A61K 8/0208; A61K 8/046; A61K 8/062; A61K 8/39; A61K 8/4973; A61K 8/604; A61K 8/86; A61K 9/0014; A61K 9/06; A61K 9/107; A61Q 17/04; A61Q 19/00; C08L 5/00
See application file for complete search history.

(56) References Cited

U.S. PATENT DOCUMENTS

| | | | |
|---|---|---|---|
| 6,831,107 B2 * | 12/2004 | Dederen ................ | A61K 8/062 424/401 |
| 7,906,664 B2 | 3/2011 | Allef et al. | |
| 7,910,119 B2 | 3/2011 | Allef et al. | |
| 8,211,972 B2 | 7/2012 | Meyer et al. | |
| 8,466,248 B2 | 6/2013 | Meyer et al. | |
| 8,653,289 B2 | 2/2014 | Wenk et al. | |
| 8,795,692 B2 | 8/2014 | Hemeyer et al. | |
| 9,427,385 B2 | 8/2016 | Meyer et al. | |
| 2006/0204468 A1 * | 9/2006 | Allef ................... | A61K 8/0208 424/70.13 |
| 2007/0092470 A1 | 4/2007 | Allef et al. | |

(Continued)

FOREIGN PATENT DOCUMENTS

| | | |
|---|---|---|
| CN | 101433500 A | 5/2009 |
| CN | 104367485 | 2/2015 |

(Continued)

OTHER PUBLICATIONS

International Search Report dated Dec. 23, 2015 in PCT/CN2015/074181 (3 pages).

(Continued)

*Primary Examiner* — Mark V Stevens
(74) *Attorney, Agent, or Firm* — Philip P. McCann; Nexsen Pruet PLLC

(57) ABSTRACT

The present invention relates to a PEG free, stable, low viscosity classic oil-in-water emulsion and the use and preparation thereof. The oil-in-water emulsion comprises, A) a primary emulsifier selected from alkyl polyglucosides and long chained polyglycerol esters, B) a secondary emulsifier selected from short chained polyglycerol esters and short chained sorbitan esters, and optionally a thickener if the amount of secondary emulsifier is below 2.5 wt. %. The emulsion is a classic emulsion and can be sprayable. The emulsion is suitable to prepare spray or foam emulsion products with good application effect.

20 Claims, 2 Drawing Sheets

(56) References Cited

U.S. PATENT DOCUMENTS

| | | |
|---|---|---|
| 2008/0004357 A1 | 1/2008 | Meyer et al. |
| 2008/0108709 A1 | 5/2008 | Meyer et al. |
| 2009/0317344 A1 | 12/2009 | Zhang et al. |
| 2010/0310617 A1 | 12/2010 | Zhang et al. |
| 2011/0028424 A1 | 2/2011 | Zhang et al. |
| 2011/0091397 A1 | 4/2011 | Zhang et al. |
| 2013/0071340 A1 | 3/2013 | Wenk et al. |
| 2013/0236561 A1 | 9/2013 | Meyer et al. |
| 2016/0340290 A1 | 11/2016 | Friedrich et al. |
| 2017/0202770 A1 | 7/2017 | Friedrich et al. |

FOREIGN PATENT DOCUMENTS

| | | |
|---|---|---|
| DE | 102008001788 A1 | 11/2009 |
| EP | 1813251 A2 | 8/2007 |
| WO | 2010063155 A1 | 6/2010 |

OTHER PUBLICATIONS

Scheuermann et al., U.S. Appl. No. 15/546,297, filed Jul. 26, 2017.
Written Opinion dated Dec. 23, 2015 in PCT/CN2015/074181 (4 pages).

\* cited by examiner

PEG FREE STABLE LOW VISCOSITY OIL-IN-WATER EMULSION AND USE THEREOF

TECHNICAL FIELD

The present invention relates to a PEG-free stable low viscosity oil-in-water emulsion and its use and preparation.

BACKGROUND ART

Nowadays, "PEG free" as a demand from both the cosmetic raw material manufacturing and the finished cosmetic product market, is clearly driving the corresponding new trend to avoid PEG, i.e. polyethylene glycol group containing ingredients. PEG materials are made from ethylene oxide, known also as EO in short, which is a petroleum derived raw material. That is already not competitive to natural based material, considering sustainability trend. Additionally, EO is a very hazardous raw material, huge caution is demanded on the manufacturing side, to minimize the risk of explosion and exposure to operational personnel. Moreover, in the field of emulsifiers and their application, performance of ethoxylated emulsifier has its weakness comparing to other emulsifiers, such as polyglycerin esters. The latter has better tolerance to electrolytes. It is also less sensitive to temperature. In optimized cases depending on the structure, the emulsification power and water resistance can be higher comparing to ethoxylated emulsifiers.

Cosmetic compositions with low viscosities have been enjoying, especially recent years, growing interest from personal care market. Such low viscosity emulsion comes with highly improved spreadability and adsorption speed. They are highly appreciated by consumers. There are many applications for stable low viscosity emulsion, for example, sprayable toner, face or body lotion, soothing lotion, sun care formulation for enhanced application properties, and so on.

The existing low viscosity emulsions mostly are oil-in-water and it is frequently sought in cosmetics due to the fact that, when applied to the skin, they give a softer, less greasy, fresher and lighter sensory than water-in-oil emulsion system, by virtue of the presence of water in the continuous outer phase.

In classical O/W emulsion systems, droplet sizes typically range between 0.5 and 20 μm. In low viscous emulsion systems, the combination of such a relatively big particle size and the density difference between internal and external phase will lead to a phase separation (tendency towards creaming of the oil droplets on top and water separation at the bottom).

The key target to obtain stable low viscous cosmetic emulsions is therefore to reduce the droplet size of cosmetic emulsions.

One option for emulsion systems with a very small droplet size are microemulsions. Different to classical emulsions, microemulsions are thermodynamically stable and have typically droplet radii of 10-40 nm which leads to clear to translucent appearance. In order to obtain such small droplets, typically high amounts of surfactants or emulsifiers are needed. A typical ratio of emulsifiers/oils for microemulsions is therefore in the range of 1/3-1/1 (B. W. Brooks, H. N. Richmond, M. Zerfa in *Modern Aspects of Emulsion Science* (Editor: B. P. Binks), Royal Society of Chemistry, Cambridge (1998)).

Different to microemulsions, nanoemulsions are just kinetically stable and the required production procedures are very specific. The conventional process for manufacturing nanoemulsions is the PIT method (Phase Inversion Temperature method) which utilizes the temperature-dependent hydrophilicity of ethoxylated emulsifiers [K. Shinoda, H. Saito, *J. Colloid Interface Sci.*, 30 (1969), 258 & T. Förster, F. Schambill, W. von Rybinski; *J. Disp. Sci. Technol.*, 13 (1992), 183]. The use of ethoxylated emulsifiers, however, is seen more and more as a disadvantage. As consumers increasingly prefer natural ingredients in cosmetics, the personal care market is extremely interested in more natural emulsions free of ethoxylated ingredients.

One option for PEG-free nanoemulsions is the so-called PIC emulsion technology which makes use of a phase inversion process at a certain water concentration upon diluting specific emulsion concentrates with water [J. Meyer, G. Polak, R. Scheuermann; *Cosmetics & Toiletries*, 122 (1) (2007), 61]. EP1813251 describes such nanoemulsions as long-term stable, low viscous systems with a small particle size that are in particular suitable for the use as impregnating lotions for wet wipes and sprayable emulsions.

One drawback of the systems described in EP1813251 is the fact that still a relatively high amount of emulsifier in relation to the oil is typically necessary in order to obtain good long term stability (typical emulsifier to oil ratio in the examples ~1/3). This limitation makes it difficult for PIC emulsions to be a commercially interesting option for O/W emulsions with an oil concentration above 10 wt. %.

CN101433500 (B) relates to a formulation of low viscosity skin lotion, the viscosities of which is ranging from 1500 mpa·s-3000 mpa·s., which is still relatively high.

US20060204468A1 described a stable PEG-free low viscosity oil-in-water emulsion. However, the emulsion is an O/W nanoemulsion which is prepared in a very specific production process via a microemulsion-like concentrate.

One of the applications of low viscosity system is to prepare spray or foam emulsion products. The lower viscosity will give better application effect on spray or pressed foam. In order to be more stable, the viscosity of spray emulsion should be increased to certain level. Then special high shearing pump will be used to make good spray or foam effect, but the cost increased undoubtedly.

So, there is an obvious and continuous need to provide stable PEG-free low viscosity oil-in-water emulsion.

SUMMARY OF THE INVENTION

The objective of the present invention is to overcome at least part of the defects of the prior art, and provide a stable low viscosity oil-in-water emulsion, which can be PEG free.

The inventors have surprisingly discovered that better stability can be obtained by using a range of PEG free oil-in-water emulsifiers, in combination with a co-emulsifier i.e., secondary emulsifier as described below, even when the viscosity of the emulsion is very low.

According to the present invention, there provides an oil-in-water emulsion, wherein the emulsion comprising,
A) a primary emulsifier selected from
  A1) alkyl polyglucosides with alkyl modifications out of the chemical class of linear or branched, saturated or unsaturated fatty alcohols with a chain length of C12 to C22, preferable of C16 to C18; and preferably the alkyl polyglucoside has a glucoside polymerization degree of >1 and ≤2, more preferable of 1.1 to 1.7; and
  A2) long chained polyglycerol esters with fatty acid moiety out of the chemical class of linear or branched, saturated or unsaturated fatty acids with a chain length of C14-C30, preferable of C15-C24, especially preferable of C16-C22; preferably the long chained polyglycerol ester has a glycerin polymerization degree of 3-15, more preferable of 4-14, especially preferable of 5-12; preferably the molar ratio of polyglycerol moiety to fatty acid moiety is in the range of 0.3-2.5, more preferably 0.4-2, most preferably 0.5-1.5;
and
B) a secondary emulsifier selected from
  B1) short chained polyglycerol esters prepared from linear or branched, saturated or unsaturated fatty acids with a chain length of C8-C12, preferably C10-C12; preferably the short chained polyglycerol ester has a glycerin polymerization degree of 2-6, more preferably 3-5; preferably the molar ratio of polyglycerol moiety to fatty acid moiety is in the range of 0.2-2, more preferably 0.3-1.8, most preferably 0.4-1.5; and
  B2) short chained sorbitan esters prepared from linear or branched, saturated or unsaturated fatty acids with a chain length of C8-C12, preferably C10-C12; preferably the molar ratio of sorbitan moiety to fatty acid moiety is in the range of 0.2-2, more preferably 0.3-1.8, most preferably 0.4-1.5;
provided that when the amount of secondary emulsifier is <2.5 wt. %, the emulsion further comprises a thickener with an amount of >0.05 wt. %, based on the total weight of the emulsion.

In some preferred embodiments, the alkyl polyglucoside has a glucoside polymerization degree of 1.2-1.4. In some preferred embodiments, the alkyl polyglucoside has a glucoside polymerization degree of 1.2-1.3. In some preferred embodiments, the long chained polyglycerol ester has a glycerin polymerization degree of 6-10. In some preferred embodiments, the molar ratio of polyglycerol moiety to fatty acid moiety is in the range of 0.7-0.9. In some preferred embodiments, the short chained polyglycerol ester has a glycerin polymerization degree of 3-6. In some preferred embodiments, the molar ratio of polyglycerol moiety to fatty acid moiety is in the range of 0.4-2, or 0.8-2. In some preferred embodiments, the molar ratio of sorbitan moiety to fatty acid moiety is in the range of 0.6-1.

When the amount of secondary emulsifier is ≥2.5 wt. %, for example, thickener is optional in the emulsion. In some embodiments, when the amount of secondary emulsifier is ≥2.5 wt. %, the emulsion does not comprise a thickener, in some embodiments, when the amount of secondary emulsifier is ≥2.5 wt. %, the emulsion also comprises a thickener.

The oil-in-water emulsion of the present invention has a low viscosity at room temperature, i.e. at 25 degrees Celsius. At the same time, it can be stable, especially in terms of phase separation. The viscosity of the oil-in-water emulsion of the present invention can be between 5 mPas and 1200 mPas, especially 5 mPas-1100 mPas, 10 mPas-1000 mPas, with the measurement using Brookfield RVT, SP04, 100 rpm, which is regarded as low viscosity in the context of the invention. The viscosity of the oil-in-water emulsion of the present invention is typically from 10 mPas to 600 mPas.

The mean droplet size of the oil-in-water emulsion of the invention is typically from 0.8 µm to 3 µm, tested by Dynamic Light Scattering Particle Size Analyzer, Horiba Model LB-500.

When the amount of secondary emulsifier is <2.5 wt. %, or ≤3.8 wt. %, and the emulsion comprises a thickener, the weight ratio of emulsifier to oil in the emulsion is typically ≤1/2.5, for example ≤1/3, ≤1/3.3, preferably <1/4 and more preferably ≤1/5, and preferably ≥1/17, for example ≥1/16, 1/15, 1/14, 1/13, or 1/12, thus low viscous emulsion systems with good long term stability can be obtained. In some embodiments, the weight ratio of emulsifier to oil in the emulsion is <1/3 and ≥1/17, preferably ≤1/3.3 and ≥1/17, or ≤1/4 and ≥1/17, more preferably ≤1/5 and ≥1/17. The weight ratio of emulsifier to oil in the emulsions is typically from 1/6 to 1/17.

When the amount of secondary emulsifier is ≥2.5 wt. % and the emulsion does not comprise a thickener, the weight ratio of emulsifier to oil in the emulsion is typically from 1:5 to 1:1, preferably from 1:4 to 1:2.5.

According to the present invention, the emulsion is preferably PEG free, i.e., one comprising no ethoxylated constituents.

According to the present invention, the emulsion is stable means that the emulsion does not show signs of instabilities like phase or water or oil separation, creaming, significant viscosity increase or decrease under the storage conditions and times, such as: 3 months storage at 25° C., 3 months storage at 45° C., three freeze thaw cycles (−15° C./25° C.).

When the amount of secondary emulsifier is <2.5 wt. %, the emulsion further comprises thickeners with an amount of ≥0.05 wt. %, for example, 0.05-0.5 wt. %, 0.055-0.5 wt. %, 0.06-0.5 wt. %, preferably 0.06-0.4 wt. %, more preferably 0.07-0.3 wt. %, or 0.05-0.2 wt. %, based on the total weight of the emulsion.

Preferably, the emulsion of the present invention is sprayable.

When the amount of secondary emulsifier is <2.5 wt. %, or ≤3.8 wt. %, and the emulsion comprises a thickener, preferably, the emulsion comprises thickeners of 0.07-0.10 wt. %, more preferably about 0.08 wt. % of carbomer, or both 0.005-0.2 wt. %, 0.02-0.1 wt. %, preferably 0.02-0.09 wt. %, 0.03-0.08 wt. %, or 0.05-0.08 wt. % of carbomer and 0.01-0.05 wt. %, more preferably 0.02-0.03 wt. %, of gellan gum, based on the total weight of the emulsion, such an emulsion has excellent sprayable property.

When the amount of secondary emulsifier is ≥2.5 wt. % and the emulsion does not comprise a thickener, preferably, the emulsion comprises 2.5-4 wt. %, more preferably 2.5-3.5 wt. % of secondary emulsifier, based on the total weight of the emulsion, such an emulsion has excellent sprayable property.

The amount of the primary emulsifier is typically from 0.1 to 6 wt. %, preferably from 0.2 to 5 wt. %, or 0.3 to 4 wt. %, especially preferable from 0.5 to 4 wt. %, or 0.5 to 3 wt. %, based on the total weight of the emulsion.

In case thickeners are included, the amount of the secondary emulsifier is typically from 0.05 to 2.5 wt. %, preferably from 0.2 to 1.8 wt. %, most preferably from 0.3 to 1.6 wt. %, based on the total weight of the emulsion.

In case no thickeners are included, the amount of the secondary emulsifier is typically from 2.5 to 5 wt. %, for example 2.5-4.5 wt. %, preferably 2.5-4 wt. %, most preferably 2.5-3.5 wt. %, based on the total weight of the emulsion.

In case thickeners are included, the amount of the oil phase is typically from 1 to 25 wt. %, preferably 3-25 wt. %, 5-25 wt. %, 5-20 wt. %, 5-18 wt. %, 10-25 wt. %, 10-20 wt. % or 10-18 wt. %, more preferably 5-15 wt. %, or 10-15 wt. %, based on the total weight of the emulsion. The amount of the oil in the emulsion is preferably from 3-22 wt. %, 5-20 wt. %, or 5-18 wt. %, particularly, the oil phase can have an oil content of ≥10 wt. %, for example, 10-20 wt. % or 10-18 wt. %, 10-15 wt. %, based on the total weight of the emulsion.

In case no thickeners are included, the amount of the oil phase is typically from 4 to 25 wt. %, preferably 5-25 wt. %, 10-25 wt %, 5-20 wt. %, 5-18 wt. %, 10-20 wt. % or 10-18 wt. %, more preferably 5-15 wt. %, or 10-15 wt. %, based on the total weight of the emulsion. The amount of the oil in the emulsion is preferably from 3-22 wt. %, 5-20 wt. %, or 5-18 wt. %, particularly, the oil phase can have an oil content of ≥10 wt. %, for example, 10-20 wt. % or 10-18 wt. %, 10-15 wt. %, based on the total weight of the emulsion.

Preferably, the emulsion does not comprise or comprise minimum amount of components that will substantially increase viscosity of the emulsion, such as for example C12-C24 alcohol, including C16-C18 alcohol.

Therefore, the present invention provides a preferably PEG free, low viscosity oil-in-water emulsion, wherein the emulsion comprising, based on the total weight of the emulsion:
A) from 0.1 to 6 wt. %, preferably from 0.2 to 5 wt. %, or 0.3 to 4 wt. %, especially preferable from 0.5 to 4 wt. %, or 0.5 to 3 wt. % of a primary emulsifier selected from
   A1) alkyl polyglucosides with alkyl modifications out of the chemical class of linear or branched, saturated or unsaturated fatty alcohols with a chain length of C12 to C22, preferable of C16 to C18; preferably the alkyl polyglucoside has a glucoside polymerization degree of of >1 and ≤2, more preferable of 1.0 to 1.7; and
   A2) long chained polyglycerol esters with fatty acid moiety out of the chemical class of linear or branched, saturated or unsaturated fatty acids with a chain length of C14-C30, preferable of C15-C24, especially preferable of C16-C22; preferably the long chained polyglycerol ester has a glycerin polymerization degree of 3-15, more preferable of 4-14, especially preferable of 5-12; preferably the molar ratio of polyglycerol moiety to fatty acid moiety is in the range of 0.3-2.5, more preferably 0.4-2, most preferably 0.5-1.5,
B) from 0.05 wt. % to 3.8 wt. %, preferably from 0.05 wt. % to 3.5 wt. %, or from 0.05 wt. % to 2.5 wt. %, more preferably from 0.2 wt. % to 1.8 wt. %, most preferably from 0.3 wt. % to 1.6 wt. % of a secondary emulsifier selected from
   B1) short chained polyglycerol esters prepared from linear or branched, saturated or unsaturated fatty acids with a chain length of C8-C12, preferably C10-C12; preferably the short chained polyglycerol ester has a glycerin polymerization degree of 2-6, more preferably 3-5; preferably the molar ratio of polyglycerol moiety to fatty acid moiety is in the range of 0.2-2, more preferably 0.3-1.8, most preferably 0.4-1.5; and
   B2) short chained sorbitan esters prepared from linear or branched, saturated or unsaturated fatty acids with a chain length of C8-C12, preferably C10-C12; preferably the molar ratio of sorbitan moiety to fatty acid moiety is in the range of 0.2-2, more preferably 0.3-1.8, most preferably 0.4-1.5;
and
C) a thickener with an amount of ≥0.05 wt. %, for example, 0.05-0.5 wt. %, 0.055-0.5 wt. %, 0.06-0.5 wt. %, preferably 0.06-0.4 wt. %, more preferably 0.07-0.3 wt. %, or 0.05-0.2 wt. %;
wherein the weight ratio of emulsifier to oil in the emulsion is ≤1/2.5, for example ≤1/3, ≤1/3.3, preferably ≤1/4, more preferably ≤1/5, or ≤1/6, and preferably ≥1/17, for example ≥1/16, 1/15, 1/14, 1/13, or 1/12.

Typically, the amount of the oil phase is from 1 to 25 wt. %, preferably 3-25 wt %, 5-25 wt %, 1-22 wt. %, 3-22 wt. %, 5-22 wt. %, 10-22 wt. %, 5-20 wt. %, 5-18 wt. %, 10-25 wt. %, 10-20 wt. % or 10-18 wt. %, more preferably 5-15 wt. %, or 10-15 wt. %.

The preferably PEG free, low viscosity oil-in-water emulsion as defined above can further comprise UV filters. Such emulsion with UV filters can also be stable with low viscosity.

Furthermore, the present invention provides a preferably PEG free, low viscosity oil-in-water emulsion, wherein the emulsion comprising, based on the total weight of the emulsion:
A) from 0.1 to 6 wt. %, preferably from 0.2 to 5 wt. %, or 0.3 to 4 wt. %, especially preferable from 0.5 to 4 wt. %, or 0.5 to 3 wt. % of a primary emulsifier selected from
   A1) alkyl polyglucosides with alkyl modifications out of the chemical class of linear or branched, saturated or unsaturated fatty alcohols with a chain length of C12 to C22, preferable of C16 to C18; preferably the alkyl polyglucoside has a glucoside polymerization degree of of >1 and ≤2, more preferable of 1.0 to 1.7; and
   A2) long chained polyglycerol esters with fatty acid moiety out of the chemical class of linear or branched, saturated or unsaturated fatty acids with a chain length of C14-C30, preferable of C15-C24, especially preferable of C16-C22; preferably the long chained polyglycerol ester has a glycerin polymerization degree of 3-15, more preferable of 4-14, especially preferable of 5-12; preferably the molar ratio of polyglycerol moiety to fatty acid moiety is in the range of 0.3-2.5, more preferably 0.4-2, most preferably 0.5-1.5;
and
B) from 2.5 wt. % to 5 wt. %, for example 2.5-4.5 wt. %, preferably from 2.5 wt. % to 4 wt. %, most preferably 2.5-3.5 wt. % of a secondary emulsifier selected from
   B1) short chained polyglycerol esters prepared from linear or branched, saturated or unsaturated fatty acids with a chain length of C8-C12, preferably C10-C12; preferably the short chained polyglycerol ester has a glycerin polymerization degree of 2-6, more preferably 3-5; preferably the molar ratio of polyglycerol moiety to fatty acid moiety is in the range of 0.2-2, more preferably 0.3-1.8, most preferably 0.4-1.5; and
   B2) short chained sorbitan esters prepared from linear or branched, saturated or unsaturated fatty acids with a chain length of C8-C12, preferably C10-C12; preferably the molar ratio of sorbitan moiety to fatty acid moiety is in the range of 0.2-2, more preferably 0.3-1.8, most preferably 0.4-1.5;
wherein the weight ratio of emulsifier to oil in the emulsion is from 1:5 to 1:1, preferably from 1:4 to 1:2.5.

Typically, the amount of the oil phase is from 4 to 25 wt. %, preferably 4-25 wt. %, 5-25 wt. %, 10-25 wt. %, 5-20 wt. %, 5-18 wt. %, 10-20 wt. % or 10-18 wt. %, more preferably 5-15 wt. %, or 10-15 wt. %, based on the total weight of the emulsion.

Primary Emulsifier

In the present patent application, the primary emulsifiers are those PEG free ones, commonly used in oil-in-water emulsions. The emulsifier is preferably a PEG free nonionic surfactant. Preferably, the HLB value is from 8-18. Examples of the primary emulsifiers include cetearyl glucoside (commercially available from Evonik with commercial name TEGO® Care CG 90), polyglyceryl-6 stearate and polyglyceryl-6 behenate (commercially available from Evonik with commercial name TEGO® Care PBS6), polyglyceryl-10 behenate/stearate, and so on. When alkyl polyglucoside is chosen as primary emulsifier, TEGO® Care CG 90, which typically has a glucoside polymerization degree of 1.0-1.7 determined according to O. Gorius et al., *Analytica Chimica Acta* 440 (2001) 231-237, is particularly preferable.

When cetearyl glucoside is used, the weight ratio of cetearyl glucoside to alcohol impurity is preferably higher than 80:20, more preferably higher than 90:10. In this regard, TEGO® Care CG 90 is preferable, which has a weight ratio of cetearyl glucoside to alcohol impurities higher than 90:10.

Secondary Emulsifier

Examples of the secondary emulsifier can be any one or more selected from the group consisting of:
polyglyceryl-3 caprate (commercially available from Evonik with commercial name TEGOSOFT® PC31),
polyglyceryl-4 caprate (commercially available from Evonik with commercial name TEGOSOFT® PC41),
polyglyceryl-4 laurate (commercially available from Evonik with commercial name TEGO® CARE PL4),
polyglyceryl-6 laurate,
polyglyceryl-6 caprylate/caprate,
polyglyceryl-3 caprylate/caprate,
sorbitan laurate (commercially available from Evonik with commercial name TEGO® SML), and
sorbitan sesquicaprylate (commercially available from Evonik with commercial name ANTIL® Soft SC).

Oil Phase

Depending on the application of the oil-in-water emulsion of the invention, the oil phase component can be cosmetic, dermatological and/or pharmaceutical oil phase components. For example, when the oil-in-water emulsion is prepared for cosmetic applications, cosmetic oils are typically used.

The oil phase components are preferable liquid. The oil phase contains at least one oil. If two or more oils are comprised in oil phase, the different oils should have good compatibility or be compatible to each other. Oil phase components of the emulsion may be selected from the group of:

1) Synthetic or naturally derived esters or ethers, for instance oils of formula RaCOORb and RaORb in which Ra represents a fatty acid residue containing from 4 to 29 carbon atoms and Rb represents a branched or unbranched hydrocarbon-based chain containing from 3-30 carbon atoms, such as, for example, diethylhexyl carbonate, C12-15 alkyl benzoate (TEGOSOFT® TN from Evonik), isopropyl palmitate, isopropyl myristate; polyol esters, for instance propylene glycol dioctanate. Natural ones such as hydrocarbon-based oils of animal and/or plant origin, including castor oil, corn oil, jojoba oil, avocado oil, caprylic/capric acid triglycerides and so on, 2) linear or branched hydrocarbons of mineral or synthetic origin which are commonly used in cosmetic field, such as, isohexadecane, mineral oil, and 3) Silicone oils which are commonly used in cosmetic field, for instance cyclomethicone; cyclohexasilxane; dimethicone (e.g., Abil®350 from Evonik) for example, the product sold under the name 200® Fluid by Dow Corning.

Oil phase can further comprise other compatible components, including but not limited to sunscreen components such as organic sun filter substances, for instance, cinnamic acid derivatives, salicylic acid derivatives, camphor derivatives, triazine derivatives, benzophenone derivatives, triazine derivatives, dibenzophenone derivatives, and p-aminobenzoic acid derivatives.

Thickeners

Thickener of the present invention can be a polymeric or nonpolymeric thickener. Examples of thickeners can be selected from the group of xanthan gum, aluminum magnesium silicate, carboxylmethyl cellulose, acacia gum (and) xanthan gum, carbomer preferably acrylates/C10-30 alkylacrylate crosspolymer, and gellan gum (high acyl). In this invention, gellan gum refers to high acyl (or HA) gellan gum. Examples of the gellan gum include gellan gum with trade name KELCOGEL® CG-HA from CP Kelco company.

Preferably, the thickener is selected from carbomer and gellan gum.

Polymeric thickeners can be chosen from following gelling agents, as examples:

1) Natural polymeric thickeners such as xanthan gum or guar gum or cellulose derivatives (such as hydroxyethylcellulose, hydroxypropylmethylcellulose, cetyl hydroxyethylcellulose), starches and alginates, preferably gellan gum which can bring quite stable emulsion with highly enhanced sprayable ability, starches and alginates, and 2) Crosslinked polymeric gelling agents such as carbomers including non-alkyl-modified carbomers and alkyl-modified carbomers such as acrylates/C10-30 alkyl acrylate crosspolymer, for example, TEGO® Carbomer 140, TEGO® Carbomer 341ER from Evonik. Moreover, polyacrylamide polymers or copolymers of acrylates, methacrylates or acrylamides with 2-acrylamido-2-methylpropanesulfonic acid (or the corresponding salts) are also suitable as polymeric thickeners.

Besides the primary emulsifier and the secondary emulsifier, the emulsion also comprises other oil phase components, and water phase components. The water phase may comprise for example, water and other compatible components including but not limited to glycol, glycerol and preservatives. Moreover the emulsion can comprise other cosmetic ingredients such as UV filters, active ingredients, film formers, preservatives, particles and sensory additives such as for instance silicon elastomer gels.

The emulsions according to the invention can comprise e.g. at least one additional component selected from the group of
emollients,
emulsifiers,
thickeners/viscosity regulators/stabilizers,
UV light protection filters,
antioxidants,
hydrotropes (or polyols),
solids and fillers,
film formers,
pearlescence additives,
deodorant and antiperspirant active ingredients,
insect repellents,
self-tanning agents,
preservatives,
conditioners,
perfumes,
dyes,
odour absorbers,
cosmetic active ingredients,
care additives,
superfatting agents,
solvents.

Substances which can be used as exemplary representatives of the individual groups are known to the person skilled in the art and can be found for example in the German application DE 102008001788.4. This patent application is herewith incorporated as reference and thus forms part of the disclosure.

As regards further optional components and the amounts of these components used, reference is made expressly to the relevant handbooks known to the person skilled in the art, e.g. K. Schrader, "Grundlagen and Rezepturen der Kosmetika [Fundamentals and Formulations of Cosmetics]", 2nd edition, pages 329 to 341, Hüthig Buch Verlag Heidelberg.

According to the present invention, the low viscosity oil-in-water emulsion of the present invention can be prepared by conventional methods in the art. In some embodiments, the preparation method comprises the steps of:
1) Heating water phase, and melting the oil phase, separately,
2) Mixing the water phase and the oil phase,
3) Homogenizing,
4) Neutralizing with sodium hydroxide (e.g., 10 wt. % aqueous solution),
5) Cooling down to room temperature whilst stirring and adding preservative below 40° C.

In some embodiments, the time of homogenization is 2 mins to 10 mins.

In some embodiments, the rate of homogenization is 7000 rpm to 14000 rpm, using handhold homogenizer ESGE-Zauberstab M122S. In some embodiments, the oil phase is heated to about 70-80° C.

According to the present invention, there provides use of the oil-in-water emulsion according to the invention for producing cosmetic, dermatological or pharmaceutical preparations, or cleaning compositions and/or care compositions for the household and industry.

The present invention provides use of the oil-in-water emulsion according to the invention for producing cosmetic, dermatological or pharmaceutical preparations, for example, the use as impregnating lotions for producing wet wipes, very particularly cosmetic wet wipes for the care and cleaning of the skin. In particular, the present invention provides use of the emulsion of the invention for producing cosmetic cleansing and/or care preparations for skin and skin appendages, for example, the use in formulations, as used, for instance, for facecare and bodycare products, babycare, sun protection preparations, makeup removers and antiperspirants/deodorants. The invention further provides the use of the emulsions for producing cleaning compositions and/or care compositions for the household and industry, such as textiles, leather, plastics, metallic and nonmetallic surfaces, for example, the use as impregnating solutions for producing wet wipes and the use in formulations.

The inventive oil-in-water emulsions are outstandingly suitable both for the production of cleaning and/or care wet wipes and for direct use in the form of emulsion systems for the cleaning and care of surfaces in the household and industry, for example, textile care, leather care, the care and cleaning of metallic or nonmetallic surfaces, for example, for the cleaning and care of automobiles or furniture.

According to the present invention, there provides a cosmetic, dermatological or pharmaceutical preparation, or cleaning preparation and/or care preparation for the household and industry, comprising the oil-in-water emulsion according to the invention. In some embodiments, the present invention provides a cosmetic cleansing and care preparation for skin and skin appendages comprising the oil-in-water emulsion according to the invention, wherein preparation can be used for instance, for facecare and bodycare products, babycare, sun protection preparations, makeup removers and antiperspirants/deodorants. In some embodiments, the emulsion of present invention is a low-viscosity sprayable sunscreen lotion. In some embodiments, the present invention provides a cleaning composition and/or care composition for the household and industry, such as textiles, leather, plastics, metallic and nonmetallic surfaces, comprising the oil-in-water emulsion of present invention.

According to the present invention, there provides a impregnated wipe or sprayable formulation, wherein the wipe or formulation comprises the oil-in-water emulsion of present invention. In some embodiments, the wipe or formulation is prepared for cosmetic use, including but not limited to use in face- and bodycare, babycare, sun protection, makeup removers, antiperspirants/deodorants. In some embodiments, the present invention provides a wet wipe, particularly cosmetic wet wipe for the care and cleaning of the skin, comprising the low viscosity oil-in-water emulsion of present invention. In some embodiments, the present invention provides a cleaning and/or care wet wipes and for direct use in the form of emulsion systems for the cleaning and care of surfaces in the household and industry, for example, textile care, leather care, the care and cleaning of metallic or nonmetallic surfaces, for example, for the cleaning and care of automobiles or furniture.

According to the present invention, there provides a cosmetic, dermatological or pharmaceutical product, or a cleaning product and/or care product for the household and industry, comprising the oil-in-water emulsion according to the invention and a package. The package can include for example, a bottle.

Therefore, the present invention provides a preferably PEG free stable oil-in-water emulsion and the use thereof. The emulsion has a very low viscosity. Preferably, the emulsion can be made as a sprayable product. In addition, the emulsion of the present invention is a classic emulsion instead of a microemulsion or nanoemulsion, thus the emulsion of the present invention can be easily prepared without requirements of any special equipment or processes. The present emulsion can have a low ratio of emulsifier to oil and low viscous lotion systems with good long term stability can be obtained. The present emulsion has good sensory. It can be widely used in cosmetics, skin care, dermatological applications, pharmaceutical, and/or home care field, such as sprayable toner, face or body lotion, soothing lotion, sun care formulation, and so on.

The oil-in-water emulsion of the present invention is suitable to prepare spray or foam emulsion products with good application effect on spray or pressed foam.

Other advantages of the present invention can be apparent to a person skilled in the art upon reading the specification of the application.

DETAILED DESCRIPTION OF THE INVENTION

The invention is now described in detail by the following examples. The scope of the invention should not be limited to the embodiments of the examples.

In the examples, TEGO® Care CG 90 was used as cetearyl glucoside, which has a glucoside polymerization degree of approximately 1.3;

TEGO® Care PBS6 was used as polyglyceryl-6 stearate and polyglyceryl-6 behenate, which has a molar ratio of polyglycerol moiety to fatty acid moiety of approximately 1:1.3;

TEGOSOFT® PC31 was used as polyglyceryl-3 caprate, which has a molar ratio of polyglycerol moiety to fatty acid moiety of approximately 1:1;

TEGO® CARE PL4 was used as polyglyceryl-4 laurate, which has a molar ratio of polyglycerol moiety to fatty acid moiety of approximately 1:1;

TEGOSOFT® PC41 was used as polyglyceryl-4 caprate, which has a molar ratio of polyglycerol moiety to fatty acid moiety of approximately 1:0.5;

TEGO® SML was used as sorbitan laurate, which has a molar ratio of sorbitan moiety to fatty acid moiety of approximately 1:1.1;

ANTIL® Soft SC was used as sorbitan sesquicaprylate, which has a molar ratio of sorbitan moiety to fatty acid moiety of approximately 1:1.5;

TEGOSOFT®TN was used as C12-15 alkyl benzoate;

TEGO® Carbomer 341ER was used as acrylates/C10-30 alkyl acrylate crosspolymer; and TEGO® Carbomer 140 was used as (non-alkyl-modified) carbomer.

Unless otherwise specified, in the examples of the description, viscosity measurement, stability test, and spray effect test were performed according to the criteria below.

Viscosity measurement: Brookfield RVT, SP04, 100 rpm.

Stability test, including: 1) storage at 45° C. for 3 months; 2) storage at 25° C. for 6 month; and 3) freeze cycles (−15° C./25° C.) for 3 times.

"Passed" means the emulsion passed stability test above and the emulsion was stable (i.e., no breaking, no separation by visual inspection). "Failed" means breaking or separation happened at one or more of the 3 kinds of stability test conditions.

Spray effect in the present invention is tested according to the following protocol:

Use a commercially available ordinary spray bottle to spray emulsions;

Spray the emulsion horizontally onto a watch glass from 15 cm in front of the surface of the watch glass, the spray direction being vertical to the surface of the watch glass; and Observe and rate the spray effect.

Figure 1:
FIG. 1 is a photo shows the effect of the emulsion with good spray effect spraying out of a spray bottle.
Figure 2:
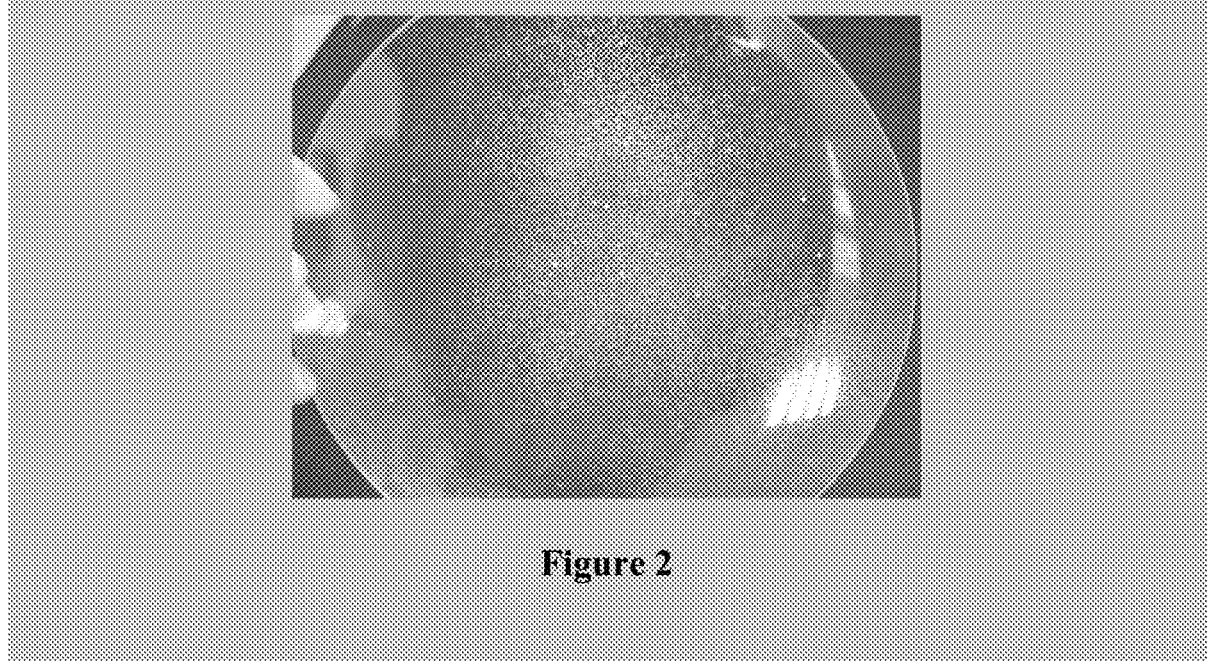
FIG. 2 is a photo shows the effect of the emulsion with good spray effect sprayed onto the surface of a wash glass.

As shown in the FIGS. 1 and 2, if fine liquid drops or nebulized drops are sprayed out of the spray bottle, and tiny and dense liquid drops are formed on the surface of the watch glass, such spray effect is rated as "good" and the emulsion with such spray effect is described as sprayable in this invention.

Figure 3:
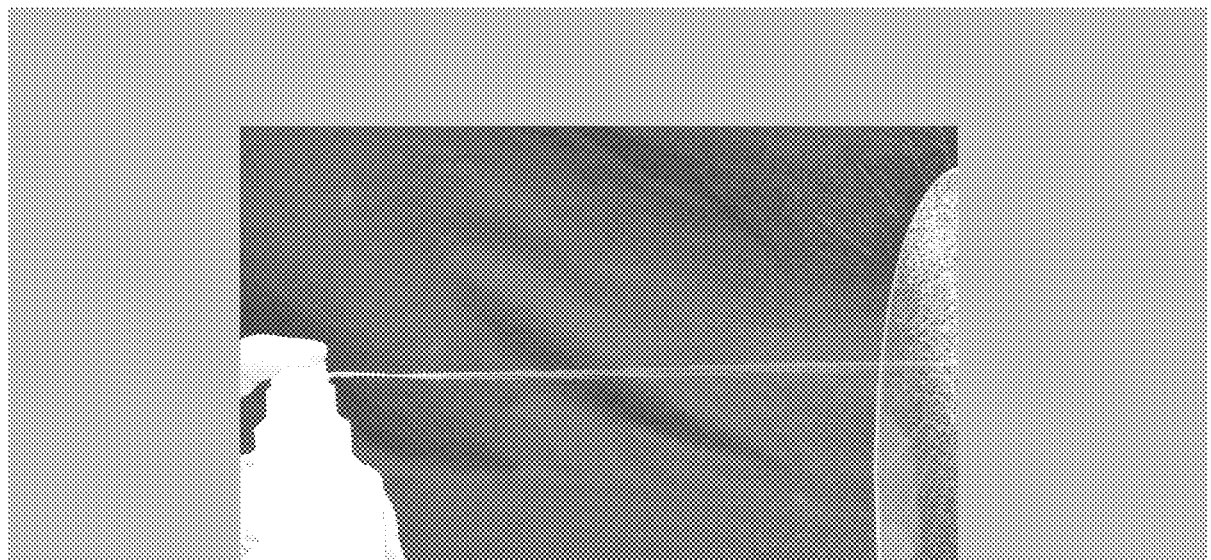
FIG. 3 is a photo shows the effect of the emulsion with poor spray effect spraying out of a spray bottle.
Figure 4:
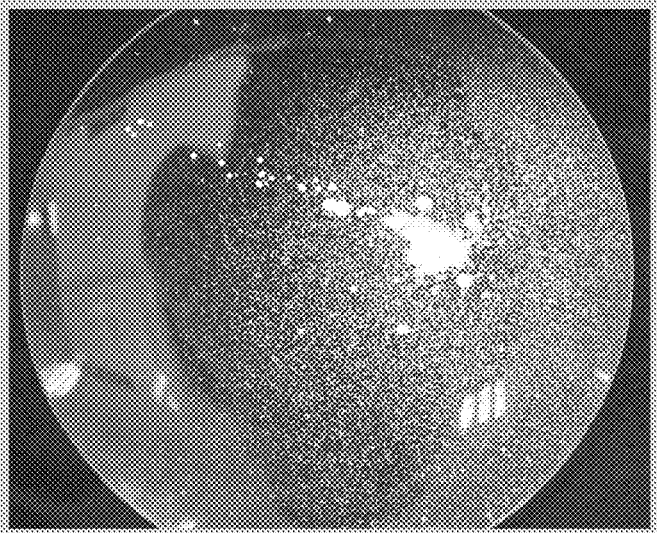
FIG. 4 is a photo shows the effect of the emulsion with poor spray effect sprayed onto the surface of a wash glass.

As shown in the FIGS. 3 and 4, if the emulsion is not nebulized, emulsion is directly ejected in the form of a thin liquid column, and the thin liquid column is splashed on the surface watch glass, such spray effect is rated as "poor" and the emulsion with such spray effect is described as not sprayable in this invention.

In the invention, the glucoside polymerization degree of an alkyl polyglucoside was determined according to the method described in O. Gorius et al., *Analytica Chimica Acta* 440 (2001) 231-237.

The average degree of polymerization N of a polyglycerol can be determined from its hydroxyl value (OHV) as follows:

$$N = \frac{(112200 - 18 \cdot OHV)}{(74 \cdot OHV - 56100)}$$

Suitable determination methods for ascertaining the hydroxyl value are those in accordance with DGF C-V 17a (53), Ph. Eur. 2.5.3 Method A and DIN 53240.

The average molecular weight of the polyglycerol can be determined from the average degree of polymerization as follows:

$$M_p = 74 \cdot N + 18$$

Where $M_p$=average molecular weight of the polyglycerol [g/mol]

N=average degree of polymerization of the polyglycerol

Synthesis of Primary Emulsifier Polyglyceryl-10 Behenate/Stearate

A mixture of glycerol (2102 g) and potassium hydroxide (24.2 g of a 45% solution in water) was heated to 240° C. within 1 h at 400 mbar and the water which was formed was continuously removed via distillation. Once the reaction mixture showed a refractive index of ≥1.4900 (typically after 20-21 h at 240° C.), the pressure was reduced to 50 mbar and the water which was formed was continuously removed together with excess glycerol via distillation until the reaction mixture showed a hydroxyl value of 880 mg KOH/g.

A mixture of a polyglycerol (396.0 g, 0.490 mol) which was obtained in the way described above, stearic acid and palmitic acid (131.8 g of a 1:1 mixture by weight, 0.489 mol), behenic acid (28.60 g, 0.083 mol) and sodium carbonate (2.75 g, 0.026 mol) was heated to 240° C. within 3 h under nitrogen sparging (nitrogen sparging was applied once the fatty acids were molten) and the water which was formed was continuously removed via distillation until the mixture showed an acid value of ≤3.

The molar ratio of polyglycerol moiety to fatty acid moiety is approximately 0.86.

Synthesis of Secondary Emulsifier Polyglyceryl-6 Laurate

A mixture of glycerol (2102 g) and potassium hydroxide (24.2 g of a 45% solution in water) was heated to 240° C. within 1 h at 400 mbar and the water which was formed was continuously removed via distillation. Once the reaction mixture showed a refractive index of ≥1.4850 (typically after 10-12 h at 240° C.), the pressure was reduced to 50 mbar and the water which was formed was continuously removed together with excess glycerol via distillation until the reaction mixture showed a hydroxyl value of 960 mg KOH/g.

A mixture of a polyglycerol (138.0 g, 0.283 mol) which was obtained in the way described above, lauric acid (62.0 g, 0.310 mol) and sodium carbonate (1.0 g, 0.009 mol) was heated to 240° C. within 3 h under nitrogen sparging (nitrogen sparging was applied once the fatty acid was molten) and the water which was formed was continuously removed via distillation until the mixture showed an acid value of ≤1.

The molar ratio of polyglycerol moiety to fatty acid moiety is approximately 0.89.

Synthesis of Secondary Emulsifier Polyglyceryl-6 Caprylate/Caprate

A mixture of glycerol (2102 g) and potassium hydroxide (24.2 g of a 45% solution in water) was heated to 240° C. within 1 h at 400 mbar and the water which was formed was continuously removed via distillation. Once the reaction mixture showed a refractive index of ≥1.4850 (typically after 10-12 h at 240° C.), the pressure was reduced to 50 mbar and the water which was formed was continuously removed together with excess glycerol via distillation until the reaction mixture showed a hydroxyl value of 960 mg KOH/g.

A mixture of a polyglycerol (222.2 g, 0.455 mol) which was obtained in the way described above, caprylic acid and capric acid (77.8 g of a 55:45 mixture by weight, 0.494 mol) and sodium carbonate (1.0 g, 0.009 mol) was heated to 240° C. within 3 h under nitrogen sparging and the water which was formed was continuously removed via distillation until the mixture showed an acid value of ≤1.

The molar ratio of polyglycerol moiety to fatty acid moiety is approximately 0.92.

Synthesis of Secondary Emulsifier Polyglyceryl-3 Caprylate/Caprate

A mixture of commercially available polyglycerol-3 (240.0 g, 0.930 mol) obtained from Solvay and caprylic acid and capric acid (78.5 g of a 55:45 mixture by weight, 0.498 mol) was heated to 240° C. within 3 h under nitrogen sparging and the water which was formed was continuously removed via distillation until the mixture showed an acid value of ≤1.

The molar ratio of polyglycerol moiety to fatty acid moiety is approximately 1.87.

Example 1: Comparison of Emulsion with Emulsifiers of Present Invention and Emulsion with PEG Containing Emulsifier Prepare the emulsion of Example 1 according to the following protocol:
1) add ingredients of phase A as defined in Table 1 into a beaker, heat the ingredients of phase A to 85° C.,
2) add ingredients of phase B into another beaker, heat the ingredients of phase B to around 85° C.,
3) mix the phase A and the phase B, and homogenize at a high speed with a homogenizer for a while,
4) add the ingredients of phase C and stir for a while, and
5) cool down with stirring, and add the ingredients of phase Z below 40° C., stir for a while until a uniform emulsion is obtained.

The other emulsions in the following examples were also prepared according to the preparation method similar to that of Example 1 above. If no phase C was added, step 4) was omitted.

TABLE 1 comparison of inventive emulsion and emulsion with PEG containing emulsifier

| | Ingredients | Comparative Example 1 wt. % | Example 1 wt. % |
|---|---|---|---|
| A | PEG-100 stearate; Glyceryl stearate | 1.5 | — |
| | cetearyl glucoside | — | 1 |
| | polyglyceryl-3 caprate | — | 0.5 |
| | C12-15 alkyl benzoate | 5 | 5 |
| | mineral oil | 5 | 5 |
| B | water | 85.76 | 85.76 |
| | acrylates/C10-30 alkyl acrylate crosspolymer | 0.08 | 0.08 |
| | Glycerin | 2 | 2 |
| C | sodium hydroxide (10 wt. % aqueous solution) | 0.16 | 0.16 |
| Z | Euxyl K350 | 0.5 | 0.5 |
| | viscosity[mPas](sp04, 100 rpm) | 1042 | 256 |
| | stability test | failed | passed |
| | spray effect | poor | good |

PEG-100 stearate; Glyceryl stearate used in the examples was the commercial available product TEGO ® Care 165 from Evonik.
Euxyl K350 was used a preservative, which has an INCI name of Phenoxyethanol/Methylparaben/Ethylparaben/Ethylhexylglycerin.

As shown in Table 1, compared with emulsion with PEG containing emulsifier (PEG-100 stearate; glyceryl stearate), emulsion of the present invention has lower viscosity, is more stable and has a better sprayable effect.

Examples 2-9: Emulsions with Different Secondary Emulsifiers

TABLE 2

Examples of different co-emulsifiers

| | Ingredients | Example 2 wt. % | Example 3 wt. % |
|---|---|---|---|
| A | cetearyl glucoside | 1 | 1 |
| | polyglyceryl-4 laurate | 0.5 | — |
| | polyglyceryl-4 caprate | — | 0.5 |
| | mineral oil | 5 | 5 |
| | C12-15 alkyl benzoate | 5 | 5 |
| B | water | To 100 | To 100 |
| | glycerin | 2 | 2 |
| | acrylates/C10-30 alkyl acrylate crosspolymer | 0.08 | 0.08 |
| C | sodium hydroxide (10 wt. % aqueous solution) | 0.16 | 0.16 |
| Z | Euxyl K350 | 0.5 | 0.5 |
| | viscosity[mPas](sp04, 100 rpm) | 184 | 206 |
| | stability test | Passed | passed |
| | spray effect | Good | good |

In Examples 2-3, the primary emulsifier is cetearyl glucoside. In example 2, the secondary emulsifier is polyglyceryl-4 laurate. In example 3, the secondary emulsifier is polyglyceryl-4 caprate.

As shown in Examples 1, 2 and 3, a sprayable, stable low viscosity emulsion system can be obtained.

TABLE 3

Examples of different co-emulsifiers

| | Ingredients | Example 4 wt. % | Example 5 wt. % | Example 6 wt. % | Example 7 wt. % | Example 8 wt. % |
|---|---|---|---|---|---|---|
| A | cetearyl glucoside | 1.3 | 1.3 | 1 | 1 | 1 |
| | sorbitan laurate | 0.5 | — | — | — | — |
| | sorbitan sesquicaprylate | — | 0.5 | — | — | — |
| | polyglyceryl-6 laurate | — | — | 0.5 | — | — |
| | polyglyceryl-6 caprylate/caprate | — | — | — | 0.5 | — |
| | polyglyceryl-3 caprylate/caprate | — | — | — | — | 0.5 |

TABLE 3-continued

Examples of different co-emulsifiers

| | Ingredients | Example 4 wt. % | Example 5 wt. % | Example 6 wt. % | Example 7 wt. % | Example 8 wt. % |
|---|---|---|---|---|---|---|
| | diethylhexyl carbonate | 7 | 7 | 7 | 7 | 7 |
| | caprylic/capric triglyceride | 7 | 7 | 7 | 7 | 7 |
| B | water | To 100 | To 100 | To 100 | To 100 | To 100 |
| | gellan gum (KELCOGEL ® CG-HA CP Kelco) | 0.03 | 0.03 | 0.03 | 0.03 | 0.03 |
| | glycerin | 2 | 2 | 2 | 2 | 2 |
| | acrylates/C10-30 alkyl acrylate crosspolymer | 0.05 | 0.05 | 0.05 | 0.05 | 0.05 |
| C | sodium hydroxide (10 wt % aqueous solution) | 0.1 | 0.1 | 0.1 | 0.1 | 0.1 |
| Z | Euxyl K350 | 0.5 | 0.5 | 0.5 | 0.5 | 0.5 |
| | viscosity[mPas] (sp04, 100 rpm) | 576 | 300 | 320 | 330 | 322 |
| | stability test | passed | passed | passed | passed | passed |
| | spray effect | good | good | good | good | good |

Gellan gum used in the examples was a product from CP Kelco company with trade name KELCOGEL ® CG-HA.

As shown in the above Tables 2 and 3, different co-emulsifiers of the present invention can achieve stable low viscosity emulsions.

Examples 9-13: Emulsions without Thickener

TABLE 4

Examples for sprayable lotion without thickener

| | Ingredients | Example 9 wt. % | Example 10 wt. % |
|---|---|---|---|
| A | cetearyl glucoside | 1 | 1 |
| | polyglyceryl-3 caprate | 3 | 3 |
| | mineral oil | 5 | — |
| | C12-15 alkyl benzoate | 5 | — |
| | diethylhexyl carbonate (TEGOSOFT ® DEC) | — | 7 |
| | caprlic/capric triglyceride (TEGOSOFT ® CT) | — | 7 |
| B | water | To 100 | To 100 |
| | glycerin | 3 | 2 |
| Z | Euxyl K350 | 0.5 | 0.5 |
| | viscosity[mPas](sp04, 100 rpm) | 12 | 10 |
| | stability test | passed | passed |
| | spray effect | good | good |

Examples 9 and 10 show that when the usage of co-emulsifier is 3 wt. %, the emulsion that has good stability in very low viscosity conditions even without any thickener and can be sprayable.

TABLE 5

Examples for sprayable lotion without thickener

| | Ingredients | Example 11 wt. % | Example 12 wt. % |
|---|---|---|---|
| A | cetearyl glucoside | 1 | 1 |
| | polyglyceryl-3 caprate | 2.5 | 3.5 |
| | diethylhexyl carbonate | 7 | 7 |

TABLE 5-continued

Examples for sprayable lotion without thickener

| | Ingredients | Example 11 wt. % | Example 12 wt. % |
|---|---|---|---|
| | caprylic/capric triglyceride | 7 | 7 |
| B | water | 80 | 79 |
| | glycerin | 2 | 2 |
| Z | Euxyl K300 | 0.5 | 0.5 |
| | viscosity[mPas](sp04, 100 rpm) | 36 | 106 |
| | stability test | passed | passed |
| | spray effect | good | good |

Euxyl K300 was used a preservative, which has an INCI name of PhenoXyaethanolum/Methylparaben/butylparaben/Ethylparaben/Propyl 4-hydroxybenzoate/isobutyl 4-hydroxybenzoate.

Examples 10-12 show that when the usage of co-emulsifier is from 2.5 wt. % to 3.5 wt. %, sprayable, stable and very low viscosity emulsion can be achieved without any thickener.

Examples 13-16: Examples for Low Viscosity Lotion with Carbomer as Thickener

TABLE 6

Sprayable skin care lotions with different amount of co-emulsifier and different amount of carbomer

| | Ingredients | Example 13 wt. % | Example 14 wt. % | Example 15 wt. % | Example 16 wt. % |
|---|---|---|---|---|---|
| A | cetearyl glucoside | 1 | 1 | 1 | 1 |
| | polyglyceryl-3 caprate | 0.05 | 0.1 | 0.2 | 0.5 |
| | C12-15 alkyl benzoate | 5 | 5 | 5 | 5 |
| | mineral oil | 5 | 5 | 5 | 5 |
| B | water | To 100 | To 100 | To 100 | To 100 |
| | acrylates/C10-30 alkyl acrylate crosspolymer | 0.08 | 0.08 | 0.08 | — |
| | (non-alkyl-modified) carbomer | — | — | — | 0.08 |
| | glycerin | 2 | 2 | 2 | 2 |
| C | sodium hydroxide (10 wt. % aqueous solution) | 0.16 | 0.16 | 0.16 | 0.16 |
| Z | Euxyl K350 | 0.5 | 0.5 | 0.5 | 0.5 |
| | viscosity [mPas] (sp04, 100 rpm) | 960 | 1146 | 768 | 194 |
| | stability test | passed | passed | passed | passed |
| | spray effect | good | good | good | good |

Example 13 shows the emulsion is stable even the amount of the co-emulsifier is only 0.05 wt. %.

Examples 13-16 show that when the amount of secondary emulsifier is <2.5 wt. %, the emulsion with 0.08 wt. % of carbomer as thickener is stable and has good spray effect.

Examples 17-24: Examples for Combination of the Emulsifiers with Different Amounts and Kinds of Oil

TABLE 7

Emulsions with different amounts of oil, used as impregnating lotion for wipes

| | Ingredients | Example 17 wt. % | Example 18 wt. % | Example 19 wt. % | Example 20 wt. % |
|---|---|---|---|---|---|
| A | cetearyl glucoside | 1 | 1 | 1 | 1 |
| | polyglyceryl-3 caprate | 0.5 | 0.5 | 0.5 | 0.5 |
| | diethylhexyl carbonate (TEGOSOFT ® DEC) | 2.5 | 5 | 7 | 9 |
| | caprylic/capric triglyceride (TEGOSOFT ® CT) | 2.5 | 5 | 7 | 9 |
| B | water | To 100 | To 100 | To 100 | To 100 |
| | gellan gum(KELCOGEL ® CG-HA CP Kelco) | — | 0.03 | 0.03 | 0.03 |
| | glycerin | 2 | 3 | 3 | 3 |
| | acrylates/C10-30 alkyl acrylate crosspolymer | 0.08 | 0.05 | 0.08 | 0.05 |
| C | sodium hydroxide (10 wt. % aqueous solution) | 0.16 | 0.1 | 0.16 | 0.1 |
| Z | Euxyl K350 | 0.5 | 0.5 | 0.5 | 0.5 |
| | viscosity [mPas] (sp04, 100 rpm) | 562 | 374 | 800 | 416 |
| | stability test | passed | passed | passed | passed |
| | spray effect | good | good | good | good |

Examples 17-20 show the gellan gum is helpful to the emulsion stability even at very low amount. And it does not have adverse influence to the spray effect.

Examples 17-20 show the combinations of the emulsifiers are compatible with different oils with different usage from 5 wt. % to 18 wt. %.

Impregnating wet wipes were prepared with emulsions in Table 7 by conventional methods.

TABLE 8

Emulsions with different kinds of oil

| | Ingredients | Example 21 wt. % | Example 22 wt. % | Example 23 wt. % | Example 24 wt. % |
|---|---|---|---|---|---|
| A | cetearyl glucoside | 1 | 1 | 1 | 1 |
| | polyglyceryl-3 caprate | 0.5 | 0.5 | 0.5 | 0.5 |
| | diethylhexyl carbonate (TEGOSOFT ® DEC) | 5 | 5 | 5 | — |
| | cetyl ricinoleate(TEGOSOFT ® CR) | 5 | — | — | — |
| | stearyl heptanoate(TEGOSOFT ® SH) | — | 5 | — | — |
| | C12-15 alkyl benzoate | — | — | 5 | 9 |
| | mineral oil | — | — | — | 9 |
| B | water | To 100 | To 100 | To 100 | To 100 |
| | acrylates/C10-30 alkyl acrylate crosspolymer | 0.05 | 0.03 | 0.05 | 0.05 |
| | gellan gum (KELCOGEL ® CG-HA CP Kelco) | 0.03 | 0.03 | 0.02 | 0.03 |
| | glycerin | 2 | 2 | 3 | 3 |
| C | sodium hydroxide (10 wt. % aqueous solution) | 0.1 | 0.06 | 0.1 | 0.1 |

TABLE 8-continued

Emulsions with different kinds of oil

| | Ingredients | Example 21 wt. % | Example 22 wt. % | Example 23 wt. % | Example 24 wt. % |
|---|---|---|---|---|---|
| Z | Euxyl K300 | 0.5 | 0.5 | 0.5 | 0.5 |
| | viscosity [mPas] (sp04, 100 rpm) | 702 | 330 | 248 | 402 |
| | stability test | passed | passed | passed | passed |
| | spray effect | good | good | good | good |

Examples 21-24 further show that the combinations of the emulsifiers are compatible with different kinds of oil.

Examples 21-24 also show that gellan gum is helpful to the emulsion stability even at very low amount. And it does not have adverse influence to the spray effect.

Examples 25-28: Examples for Different Amount of Primary Emulsifier

TABLE 9

Emulsions with different amount of primary emulsifier

| | Ingredients | Example 25 wt. % | Example 26 wt. % | Example 27 wt. % | Example 28 wt. % |
|---|---|---|---|---|---|
| A | cetearyl glucoside | 0.5 | 1 | 1.5 | 2 |
| | polyglyceryl-3 caprate | 0.5 | 0.5 | 0.5 | 0.5 |
| | C12-15 alkyl benzoate | 7 | 7 | 7 | 7 |
| | mineral oil | 7 | 7 | 7 | 7 |
| B | water | To 100 | To 100 | To 100 | To 100 |
| | acrylates/C10-30 alkyl acrylate crosspolymer | 0.05 | 0.05 | 0.05 | 0.05 |
| | gellan gum(KELCOGEL ® CG-HA CP Kelco) | 0.03 | 0.03 | 0.03 | 0.03 |
| | glycerin | 2 | 2 | 2 | 2 |
| C | sodium hydroxide (10 wt. % aqueous solution) | 0.1 | 0.1 | 0.1 | 0.1 |
| Z | Euxyl K300 | 0.5 | 0.5 | 0.5 | 0.5 |
| | viscosity [mPas] (sp04, 100 rpm) | 390 | 486 | 522 | 804 |
| | stability test | passed | passed | passed | passed |
| | spray effect | good | good | good | good |

Examples 25-28 show that the emulsions with different amount of primary emulsifier are stable.

Examples 29-32: Emulsifiers with Different Kinds of Oil

TABLE 10

Ultra-low viscous sprayable emulsions without polymeric thickener

| | Ingredients | Example 29 wt. % | Example 30 wt. % | Example 31 wt. % | Example 32 wt. % |
|---|---|---|---|---|---|
| A | cetearyl glucoside | 1 | 1 | 1 | 1 |
| | polyglyceryl-3 caprate | 3 | 3 | 3 | 3 |
| | diethylhexyl carbonate (TEGOSOFT ® DEC) | 5 | — | — | 4.5 |
| | phenoxyethyl caprate (TEGOSOFT ® XC) | 5 | 5 | — | — |

TABLE 10-continued

Ultra-low viscous sprayable emulsions without polymeric thickener

| | Ingredients | Example 29 wt. % | Example 30 wt. % | Example 31 wt. % | Example 32 wt. % |
|---|---|---|---|---|---|
| | C12-15 alkyl benzoate | — | 5 | 5 | — |
| | isopropyl myristate(TEGOSOFT ® M) | — | — | 5 | — |
| | caprylic/capric triglyceride (TEGOSOFT ® CT) | — | — | — | 4.5 |
| | dimethicone(ABIL ® 350) | — | — | — | 1 |
| B | water | To 100 | To 100 | To 100 | To 100 |
| | glycerin | 3 | 3 | 3 | 3 |
| Z | Euxyl K350 | 0.6 | 0.6 | 0.6 | 0.6 |
| | viscosity [mPas] (sp04, 100 rpm) | 36 | 42 | 36 | 16 |
| | stability test | passed | passed | passed | passed |
| | spray effect | good | good | good | good |

Examples 29-32 further show that different kinds of oil can be used in the emulsion of the present invention. Examples 29-32 show that when the amount of the secondary emulsifiers is around 3 wt. % stable emulsions with super low viscosity and very good spray effect can be obtained.

Examples 33-35: Emulsion with the Ingredients of UV Filters

TABLE 11

Comparative example and Example 33 for low viscosity sunscreen lotion

| | Ingredients | Comparative Example 2 wt. % | Example 33 wt. % |
|---|---|---|---|
| A | PEG-100 stearate; Glyceryl stearate | 1.5 | — |
| | cetearyl glucoside | — | 1 |
| | polyglyceryl-3 caprate | — | 0.5 |
| | ethylhexyl triazone | 1.5 | 1.5 |
| | ethylhexyl methoxycinnamate | 8 | 8 |
| | 4-methylbenzylidene camphor | 2 | 2 |
| | cyclopentasiloxane (and) cyclohexasiloxane | 5 | 5 |
| | C12-15 alkyl benzoate | 3.5 | 3.5 |
| B | water | To 100 | To 100 |
| | glycerin | 2 | 2 |
| | acrylates/C10-30 alkyl acrylate crosspolymer | 0.03 | 0.03 |
| | gellan gum (KELCOGEL ® CG-HA CP Kelco) | 0.03 | 0.03 |
| C | sodium hydroxide (10 wt. % aqueous solution) | 0.06 | 0.06 |
| Z | Euxyl K300 | 0.5 | 0.5 |
| | viscosity [mPas] (sp04, 100 rpm) | 228 | 234 |
| | stability test | failed | passed |
| | SPF value(EU, Colipa)*** | 14.1 | 14.1 |

***SPF (international method): BASF sunscreen Simulator.

Example 33 shows the low viscosity emulsion with UV filter ingredients is stable. While Comparative Example 2 shows that the emulsion with PEG containing emulsifier cannot be stable under the same condition.

TABLE 12

Low-viscosity sunscreen lotions SPF 30 and SPF 50

| | Ingredients | Example 34 wt. % | Example 35 wt. % |
|---|---|---|---|
| A | polyglyceryl-10 behenate/stearate | 3 | 3 |
| | polyglyceryl-3 caprate | 0.5 | 0.5 |
| | C12-15 alkyl benzoate | 5.9 | 5.9 |
| | BEMT (Tinosorb S, BASF SE) | 2 | 4 |
| | BMDM | 2 | 5 |
| | ethylhexyl salicylate | 2 | 4 |
| | ethylhexyl triazone (Uvinul T150. BASF SE) | 1 | 2 |
| | octocrylene | 5 | 7 |
| B | water | To 100 | To 100 |
| | glycerin | 2 | 2 |
| | carbomer (TEGO ® Carbomer 141) | 0.2 | 0.2 |
| | xanthan gum (Keltrol CG-SFT, CP Kelco) | 0.1 | 0.1 |
| C | NaOH 10% aq. | 0.4 | 0.4 |
| | PBSA (20% aq., neutralized w. NaOH) (Eusolex 232, Merck KGaA) | — | 20 |
| | PBSA (10% aq., neutralized w. NaOH) (Eusolex 232, Merck KGaA) | 20 | — |
| | ethanol | 7 | 7 |
| Z | preservative (Euxyl PE 9010. Schuelke & Mayr) | 0.7 | 0.7 |
| | viscosity[mPas] (Brookfield sp4 100 rpm) | 400 | 450 |
| | stability test | passed | passed |
| | SPF (EU, Colipa)*** | 30 | 50 |

***SPF (international method): BASF sunscreen Simulator

In Table 12, BEMT represents bis-ethylhexyloxyphenol methoxyphenyl triazine, BMDM represents butyl methoxydibenzoylmethane, and PBSA represents phenylbenzimidazole sulfonic acid.

Example 34 shows the low viscosity emulsion of the present invention with UV filter ingredients is stable with SPF value of 30 (calculated by BASF sunscreen Simulator).

Example 35 shows the low viscosity emulsion with UV filter ingredients is stable and can obtain high SPF value of 50 (calculated by BASF sunscreen Simulator).

Examples 36-37: Emulsions with Polyglyceryl-6 Stearate and Polyglyceryl-6 as Primary Emulsifier

TABLE 13

Low-viscosity emulsion

| | Ingredients | Example 36 wt. % | Example 37 wt. % |
|---|---|---|---|
| A | polyglyceryl-6 stearate and polyglyceryl-6 behenate | 1 | 2 |
| | polyglyceryl-3 caprate | 0.5 | 0.5 |
| | mineral oil | 5 | 5 |
| | C12-15 alkyl benzoate | 5 | 5 |
| B | water | To 100 | To 100 |
| | glycerin | 3 | 3 |
| | acrylates/C10-30 alkyl acrylate crosspolymer | 0.08 | 0.08 |
| C | sodium hydroxide (10 wt. % aqueous solution) | 0.16 | 0.16 |
| Z | Euxyl K350 | 0.5 | 0.5 |
| | viscosity[mPas](sp04, 100 rpm) | 250 | 358 |
| | stability test | passed | passed |
| | spray effect | good | good |

In Examples 36-37, the primary emulsifier is polyglyceryl-6 stearate and polyglyceryl-6 behenate.

As used herein, the phrases "include", "selected from", and the like includes mixtures or combinations of the specified materials. Terms such as "contain(s)" and the like as used herein are open terms meaning "including at least" unless otherwise specifically noted.

All references, patents, applications, tests, documents, publications, texts, articles, etc. mentioned herein are incorporated herein by reference. Unless otherwise explicitly specified, where a numerical limit or range is stated, the endpoints are included, and all values and sub ranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. An oil-in-water emulsion, comprising,
A) from 0.1 to 6 wt % based in the total weight of the oil-in-water emulsion of a primary emulsifier selected from the group consisting of
A1) alkyl polyglucosides with alkyl modifications out of the chemical class of linear or branched, saturated or unsaturated fatty alcohols with a chain length of C16 to C18 wherein the alkyl polyglucoside has a glucoside polymerization degree of from 1.0 to 1.7; and
A2) long chained polyglycerol esters with fatty acid moiety out of the chemical class of linear or branched, saturated or unsaturated fatty acids with a chain length of C16-C22; wherein the long chained polyglycerol ester has a glycerin polymerization degree of 5-12; wherein the molar ratio of polyglycerol moiety to fatty acid moiety is in the range of 0.3-2.5; and
B) from 0.05 to less than 2.5 wt % based in the total weight of the oil-in-water emulsion of a secondary emulsifier selected from the group consisting of
B1) short chained polyglycerol esters prepared from linear or branched, saturated or unsaturated fatty acids with a chain length of C8-C12; wherein the short chained polyglycerol ester has a glycerin polymerization degree of 3-5; and wherein the molar ratio of polyglycerol moiety to fatty acid moiety is in the range of 0.2-2; and
B2) short chained sorbitan esters prepared from linear or branched, saturated or unsaturated fatty acids with a chain length of C8-C12; wherein the molar ratio of sorbitan moiety to fatty acid moiety is in the range of 0.2-2;
provided that the emulsion further comprises a thickener with an amount of ≥0.05 wt. %, based on the total weight of the oil-in-water emulsion
wherein the oil-in-water emulsion does not include C12-C24 alcohol and the viscosity of the oil-in-water emulsion is between 5 mPas and 1200 mPas, with the measurement using Brookfield RVT, SP04, 100 rpm.

2. The oil-in-water emulsion of claim 1, wherein the viscosity of the oil-in-water emulsion is between 10 mPas and 1000 mPas, with the measurement using Brookfield RVT, SP04, 100 rpm.

3. The oil-in-water emulsion of claim 1, wherein the mean droplet size of the oil-in-water emulsion is from 0.8 μm to 3 μm.

4. The oil-in-water emulsion of claim 1, wherein the weight ratio of emulsifier/oil in the emulsion is ≤1/2.5.

5. The oil-in-water emulsion of claim 1, wherein the emulsion is PEG free.

6. The oil-in-water emulsion of claim 1, wherein the emulsion is sprayable.

7. The oil-in-water emulsion of claim 1, wherein the emulsion comprises thickeners of from 0.07-0.10 wt. % of carbomer and from 0.01-0.05 wt. % of gellan gum, the wt % based on the total weight of the emulsion.

8. The oil-in-water emulsion of claim 1, wherein the secondary emulsifier is selected from the group consisting of polyglyceryl-3 caprate, polyglyceryl-4 caprate, polyglyceryl-4 laurate, polyglyceryl-3 caprylate/caprate, sorbitan laurate, sorbitan sesquicaprylate, and any mixtures thereof.

9. A cosmetic, dermatological or pharmaceutical preparation, or cleaning preparation and/or care preparation for the household and industry, comprising the oil-in-water emulsion of claim 1.

10. A cosmetic, dermatological or pharmaceutical product, or a cleaning product and/or care product for the household and industry, comprising the oil-in-water emulsion of claim 1 and a package.

11. The oil-in-water emulsion of claim 1, wherein the long chained polyglycerol ester has a glycerin polymerization degree of 5-12; wherein the molar ratio of polyglycerol to fatty acid moiety is in the range of 0.4-2; and
B) a secondary emulsifier selected from the group consisting of
B1) short chained polyglycerol esters prepared from linear or branched,
saturated or unsaturated fatty acids with a chain length of C10-12; wherein the short chained polyglycerol ester has a glycerin polymerization degree of 3-5; wherein the molar ratio of polyglycerol moiety to fatty acid moiety is in the range of 0.3-1.8; and
B2) short chained sorbitan esters prepared from linear or branched, saturated or unsaturated fatty acids with a chain length of C10-12; wherein the molar ratio of sorbitan moiety to fatty acid moiety is in the range of 0.3-1.8,
wherein the oil-in-water emulsion does not include C12-C24 alcohol and the viscosity of the oil-in-water emulsion is between 5 mPas and 1000 mPas, with the measurement using Brookfield RVT, SP04, 100 rpm.

12. The oil-in-water emulsion of claim 11, wherein the viscosity of the oil-in-water emulsion is between 10 mPas and 600 mPas, with the measurement using Brookfield RVT, SP04, 100 rpm.

13. The oil-in-water emulsion of claim 12, wherein the mean droplet size of the oil-in-water emulsion is from 0.8 μm to 3 μm.

14. The oil-in-water emulsion of claim 11, wherein the weight ratio of emulsifier/oil in the emulsion is less than 1/4.

15. The oil-in-water emulsion of claim 11, wherein the weight ratio of emulsifier/oil in the emulsion is less than 1/5.

16. The oil-in-water emulsion of claim 11, wherein the emulsion is PEG free.

17. The oil-in-water emulsion of claim 11, wherein the emulsion is sprayable.

18. The oil-in-water emulsion of claim 11, wherein the emulsion comprises thickeners of 0.07-0.10 wt. % of carbomer and 0.01-0.05 wt. % of gellan gum.

19. The oil-in-water emulsion of claim 11, wherein the emulsion comprises thickeners of 0.02-0.1 wt. % of carbomer and 0.01-0.05 wt. % of gellan gum.

20. The oil-in-water emulsion of claim 11, wherein the secondary emulsifier is selected from the group consisting of: polyglyceryl-3 caprate, polyglyceryl-4 caprate, polyglyceryl-4 laurate, polyglyceryl-3 caprylate/caprate, sorbitan laurate, sorbitan sesquicaprylate, and any mixtures thereof.

* * * * *

UNITED STATES PATENT AND TRADEMARK OFFICE
CERTIFICATE OF CORRECTION

PATENT NO. : 10,292,925 B2
APPLICATION NO. : 15/549183
DATED : May 21, 2019
INVENTOR(S) : Yinghua Gu et al.

It is certified that error appears in the above-identified patent and that said Letters Patent is hereby corrected as shown below:

In the Claims

Column 22,
Line 57, Claim 13, "emulsion of claim 12" should read -- emulsion of claim 11 --.

Signed and Sealed this
Second Day of July, 2019

Andrei Iancu
*Director of the United States Patent and Trademark Office*